United States Patent [19]

Speaker

[11] 4,453,933
[45] Jun. 12, 1984

[54] INTRAVENOUS DEVICE

[76] Inventor: Mark G. Speaker, 145 E. 16th St., Apt. 20C, New York, N.Y. 10003

[21] Appl. No.: 324,542

[22] Filed: Nov. 24, 1981

[51] Int. Cl.³ .............................................. A61M 5/00
[52] U.S. Cl. .................................... 604/179; 128/133; 128/DIG. 26
[58] Field of Search ....... 128/214, 133, 132, DIG. 26, 128/207.15, 348; 604/174, 179

[56] References Cited

U.S. PATENT DOCUMENTS

| | | |
|---|---|---|
| 503,973 | 8/1893 | Lovejoy . |
| 2,135,086 | 11/1938 | Marton . |
| 2,259,817 | 10/1941 | Hawkins . |
| 2,266,231 | 12/1941 | Mazzeo et al. ............. 128/DIG. 26 |
| 2,409,432 | 10/1946 | Hubbard . |
| 2,418,561 | 4/1947 | Stallcup . |
| 2,449,882 | 9/1948 | Daniels . |
| 2,525,398 | 10/1950 | Collins . |
| 2,533,961 | 12/1950 | Rousseau et al. . |
| 2,669,231 | 2/1954 | Fisher . |
| 3,059,645 | 10/1962 | Hasbrouck et al. . |
| 3,194,235 | 7/1965 | Cooke . |
| 3,196,870 | 7/1965 | Sprecher et al. . |
| 3,722,508 | 3/1973 | Roberts . |
| 3,765,421 | 10/1973 | Poprik . |
| 3,782,378 | 1/1974 | Page . |
| 3,812,851 | 5/1974 | Rodriquez . |
| 3,901,226 | 8/1975 | Scardenzan . |
| 3,957,048 | 5/1976 | Jacobs . |
| 4,059,105 | 11/1977 | Cutruzzula . |
| 4,088,136 | 5/1978 | Hasslinger et al. . |
| 4,096,863 | 6/1978 | Kaplan et al. . |
| 4,198,989 | 4/1980 | Hawke et al. . |
| 4,316,461 | 2/1982 | Marais et al. ............... 128/DIG. 26 |

Primary Examiner—Stephen C. Pellegrino
Attorney, Agent, or Firm—Kenyon & Kenyon

[57] ABSTRACT

A device and a method for feeding a patient intravenously in a manner that reduces the potential for interruption of the intravenous therapy. The device includes an adjustable strap with fastening means for loosely securing the strap around a patient's limb. The encircling length of the strap is adjusted such that the strap is permitted to move longitudinally along the limb where the natural contours of the limb prevent removal of the strap from the limb, and the natural contours preferably stop the longitudinal movement of the strap short of an intended infusion site on the limb. An intravenous feeding tube is affixed to the strap at a location intermediate the ends of the tube, the segment of tubing between the strap and the catheter end of the tube having sufficient slack such that the longitudinal movement of the strap away from the infusion site will be stopped by the contours of the patient's limb before all of the slack is used. Further, a protection sleeve is provided for inserting and covering the patient's limb, with the protection sleeve being connectable to the strap to isolate the strap and the infusion site so as to prevent patient access thereto.

19 Claims, 9 Drawing Figures

Fig.4.

INTRAVENOUS DEVICE

BACKGROUND OF THE INVENTION

1. Field of the Invention

This invention relates to a device and a method for feeding a patient intravenously in a manner that reduces the potential for active and passive interruption of the intravenous therapy except as authorized by medical personnel.

2. Prior Art

After a catheter is inserted into a patient's vein, the catheter and its associated tubing are commonly taped to the patient to maintain the catheter in position. Unfortunately, such taping is of limited effectiveness. Many patients move in a manner which inadvertantly pulls on the tubing. Sometimes the tubing is accidently pulled by those near the patient, as, or example, by someone changing the bedclothes. Such pulling often entirely removes the catheter from the vein or tears the vein in which the catheter lies, thereby interrupting the intravenous therapy in all too often critical situations. Further, when the vein is torn, painful infiltration of fluid into the surrounding tissue results.

While it is often difficult to maintain intravenous feeding of cooperative patients, many demented or injured patients, unknowingly and sometimes intentionally, will often pull the catheter from their bodies, thereby denying themselves lifesaving fluid. Unfortunately, in such cases, the patients must be fully restrained in their beds in order to conduct intravenous feeding. This is certainly an uncomfortable and undesirable situation.

When the catheter is pulled and results in either full removal of the catheter, or disruption of the wall of the vein, medical personnel must first become aware of the problem and then locate another vein and re-insert the cathether. The number of veins available for intravenous therapy is, however, limited by both the state of health of the patient and the number of veins already damaged by previous cathether insertions. It is often difficult, therefore, to re-insert a catheter into a patient who is in poor health or who has undergone extended intravenous therapy.

Thus, it is clearly undesirable to allow situations where the patient's catheter might be pulled upon: the patient's health is endangered; the patient is subjected to pain associated with fluid infiltration into the surrounding tissue; the patient is subjected to pain associated with re-insertion of the cathether; and medical staff is diverted from other important duties.

The prior art has attempted many means of overcoming the ineffectiveness of tape in maintaining a catheter in a patient's vein. These devices utilize a strap of some sort tightly secured around the patient's limb, with the catheter and/or its tubing attached to the strap. Examples of such devices are those shown in U.S. Pat. No. 3,812,851 and U.S. Pat. No. 3,765,421. Even slight constriction of a limb by such devices, however, creates a tourniquet effect, slowing and often stopping flow in the veins. Restriction of flow in the veins promotes blood coagulation in the catheter and elevates the pressure in the vein, which thereby promotes tearing of the vessel wall. A constricting band can therefore render the vein, and the catheter inserted therein, useless for further fluid administration.

Flexure of a joint may also restrict venous flow. The prior art has, therefore, utilized devices to restrict flexure of the patient's limb during intravenous feeding. Illustrative devices are shown in U.S. Pat. No. 3,812,851 and U.S. Pat. No. 3,722,508. These prior art devices are, however, constricting and very uncomfortable for the patient. Further, in order to be effective, they must usually closely fit the contours of the limb to which they are to be attached. Hence, it is necessary that many different sizes and shapes of any particular device be available, in order to accomodate not only persons of different dimensions in both the adult and pediatric populations, but also the right and left limbs of such diverse populations. The means most commonly used to prevent flexure of a patient's limb is a padded splint taped tightly to the limb. This is commonly known as an arm board.

The prior art devices used to maintain the cathether in position and to restrict limb flexure greatly limit the number and the location of potential catheter insertion sites by covering a significant portion of the limb. Such a limitation may not be tolerable for a patient having few available veins or requiring extended intravenous therapy.

SUMMARY OF THE INVENTION

In accordance with the device and the method of the present invention, there is provided an adjustable strap with fastening means for loosely securing the strap around a patient's limb. The encircling length of the strap is adjusted such that the strap is permitted to move longitudinally along the limb where the natural contours of the limb prevent removal of the strap from the limb, and the natural contours preferably stop the longitudinal movement of the strap short of an intended infusion site on the limb. An intravenous feeding tube is affixed to the strap at a location intermediate the ends of the tube, the segment of tubing between the strap and the catheter end of the tube having sufficient slack such that the longitudinal movement of the strap away from the infusion site will be stopped by the contours of the patient's limb before all of the slack is used. Further, a protection sleeve is provided for inserting and covering the patient's limb, with the protection sleeve being connectable to the strap to isolate the strap and the infusion site so as to prevent patient access thereto.

DETAILED DESCRIPTION OF THE DRAWINGS

Figures 1, 2, 3:
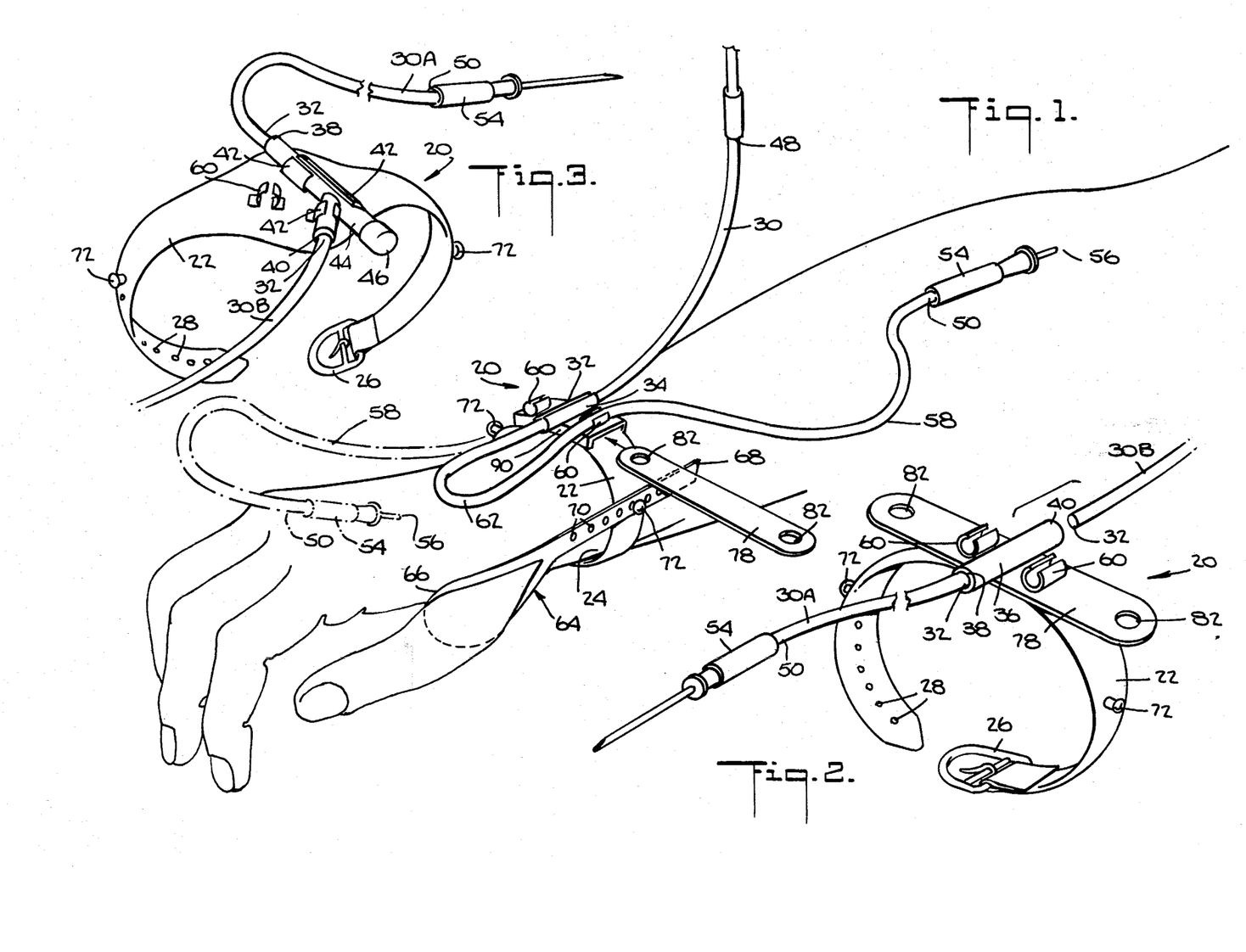
FIG. 1 illustrates an intravenous feeding device attached to a patient's wrist.
FIG. 2 illustrates another embodiment of the intravenous feeding device of FIG. 1.
FIG. 3 illustrates still another embodiment of the intravenous feeding device of FIG. 1.

Referring now to the various figures of the drawings where like reference characters refer to like parts, there is shown in FIG. 1 an intravenous feeding device 20. Device 20 comprises a strap 22 having affixed thereto tube 30.

Strap 22 is adapted for loose securement around the patient's limb as illustrated by the space 24 between the strap 22 and the patient's wrist shown in FIG. 1. Such loose securement can be achieved by a variety of means. As shown in FIG. 2, one means of achieving this loose securement is the use of a buckle 26 attached to one end of the strap 22 for connection with one of a plurality of holes 28 in the other end of the strap 22. With such construction, medical personnel can place the strap 22 around the patient's limb and and adjust the encircling length of the strap so as to allow longitudinal movement of the strap 22 along the patient's limb. The encircling length of the strap 22 must further be adjusted such that the natural contours of the limb prevent removal of the strap from the limb. Such loose securement of strap 22 around the patient's limb does not constrict the patient's veins as does the tightly fitting bands of the prior art.

As used herein, reference to longitudinal movement means movement along the patient's limb from a proximal part of the limb, e.g., the upper part of the arm, to a distal part of the limb, e.g., the forearm, and vice versa.

Returning to FIG. 1, there is shown tube 30 affixed to the strap 22 at a location 32 intermediate the ends of the tube 30. Intermediate location 32 of the tube 30 is shown in FIG. 1 affixed to the strap 22 by a pair of complementary upstanding posts 34. Posts 34 press against the tube 30 in a manner such that friction forces prevent the tube 30 from sliding relative to the strap 22. Preferably posts 34 include means (not shown), such as a small overlying strap or a set-screw, to further secure tube 30 in place and to prevent separation of tube 30 from the strap 22 by a pull on the tube directed vertically away from the strap.

FIG. 2 illustrates a preferred embodiment of affixing the tube 30 to the strap 22. Affixed to the strap 22 is a tubular connecting means 36, which is capable of fluid flow therethrough. The tubular connecting means 36 has a first tubular connecting site 38 and a second tubular connecting site 40. Tube 30 is severed into two segments, 30A and 30B. Tube segment 30A is securely connected to the tubular connecting means 36 at the tubular connecting site 38. Tube segment 30B is securely connected to the tubular connecting means 36 at the tubular connecting site 40. For additional security, an adhesive material can be added at the tubular connecting sites 38 and 40 to more firmly affix the tube segments 30A and 30B to the tubular connecting means 36.

Another preferred embodiment of affixing the tube 30 to the strap 22 is illustrated in FIG. 3. Affixed to the strap 22 is a plurality of upstanding posts 42 for engaging and receiving a Y-connector 44. The Y-connector 44 has the tubular connecting sites 38 and 40 for securely connecting thereto the tube segments 30A and 30B, respectively, of tube 30. Again, adhesive material can be used at the tubular connecting sites 38 and 40. The Y-connector 44 is snapped into the posts 42 where it is firmly held in place by the posts 42. Preferably, posts 42 include means (not shown), such as a small overlying strap or a set-screw, to further secure the Y-connector 44 and tube 30 in place and to prevent separation of tube 30 from the strap 22 by a pull on the tube directed vertically away from the strap. The use of Y-connector 44 is not only convenient for purposes of the present invention, but also provides a site 46 for injection of any additionally required medicinal fluids without the need for separate injection into the patient's tissue.

Returning then to FIG. 1, tube 30 has ends 48 and 50. The end 48 of tube 30 is connected to a fluid reservoir 52 (shown in FIG. 4), from which the intravenous fluid is fed to the patient. The end 50 of the tube 30 is connected to a catheter 54 for insertion into a vein on the patient's limb at an infusion site 56. The infusion site 56 can be located essentially anywhere on the limb, for example, on the patient's arm or on the patient's hand, as illustrated alternatively in FIG. 1.

As used herein, reference to a patient's limb includes the patient's arms as well as the patient's legs.

Between the intermediate location 32 affixed to the strap 22 and the cathether end 50 of the tube 30, the tube 30 must have sufficient slack 58 therein such that the longitudinal movement of the strap 22 away from the infusion site 56 will be stopped by the natural contours of the patient's limb before all of the slack 58 is used. For example, when the infusion site 56 is on the patient's hand, as illustrated in one embodiment of FIG. 1, there must be sufficient slack 58 in the tube 30 such that all of the slack 58 is not used when the strap 22 moves or is pulled proximally up the patient's arm toward the trunk of the patient's body. The strap 22 reaches a point on the limb where the natural contours of the limb prevents further proximal movement of the strap. When strap 22 reaches such point, tube 30 still has some slack 58 therein. Hence, no dislodging tension or force can transmitted through the strap 22 to the catheter 54 at the infusion site 56. As another example, when the infusion site 56 is on the patient's arm, as illustrated in the second embodiment in FIG. 1, there must be sufficient slack 58 in the tube 30 such that all of the slack 58 is not used when the strap 22 moves or is pulled distally down to the patient's wrist, where the natural contours of the patient's hand and wrist prevents removal of the strap from the limb. When strap 22 reaches such point, tube 30 still has some slack 58 therein, and again, no dislodging tension or force can be transmitted through the strap 22 to the catheter 54 at the infusion site 56.

The encircling length of strap 22 is preferably adaptable to a position such that, when the strap 22 is secured around the patient's limb, the natural contours of the limb restricts the longitudinal movement of the strap 22 toward the infusion site 56 before the strap can reach and interfere with the intravenous feeding.

The strap 22 having an adaptable encircling length, in conjunction with the slack 58 in the tube 30, provides an effective means of maintaining the catheter 54 inserted at the infusion site 56. The patient is free to move the limb with little concern that a pull on or movement of the tube 30 between the fluid reservoir end 48 and the intermediate point 32 might dislodge the catheter 54 from the infusion site 56. Any tension applied to tube 30 between the fluid reservoir end 48 and the intermediate point 32 is transmitted to the strap 22 and then to the patient's limb and not to the catheter 54.

Figure 4:
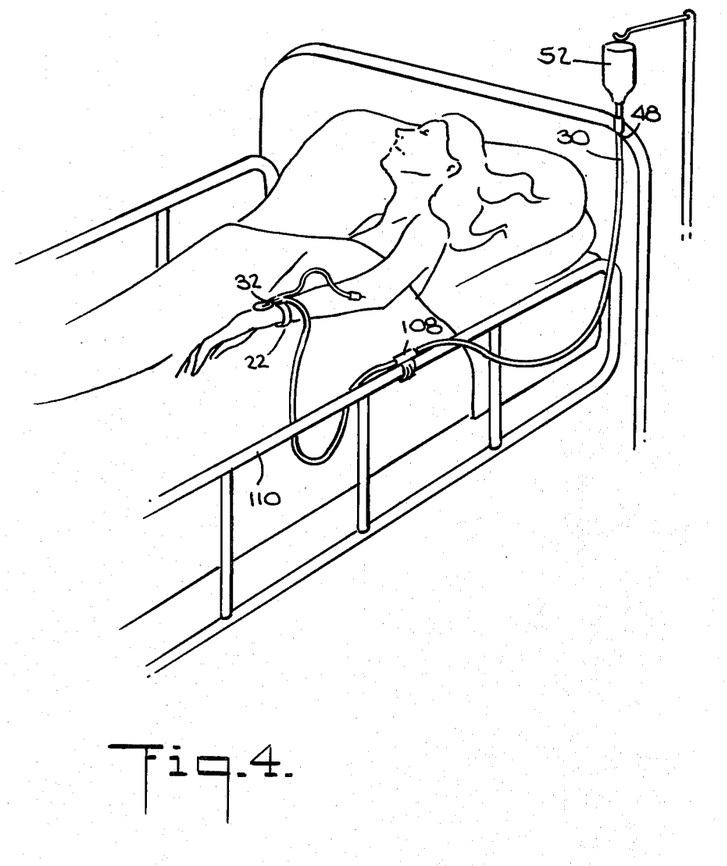
FIG. 4 illustrates the use of a strap to secure a patient's intravenous tubing to the rails on a hospital bed.

Preferably, the device 20 has affixed thereto a plurality of upstanding posts 60 for receiving and engaging the tube 30. Posts 60 are useful for holding tube 30 at any point therealong that has excess slack therein. Posts 60 are particularly useful for holding tube 30 when it is necessary that the physical direction of tube 30 be doubled back so as to accommodate the infusion site 56, as shown by the doubling back of tube segment 62 along tube 30 in FIG. 1. This is particularly useful when the fluid reservoir is located generally behind the patient as shown in FIG. 4. Posts 60 should not be used in a manner which interferes with the required slack 58. For example, when tube 30 is doubled back at a point between the intermediate location 32 and the catheter end 50 of the tube 30 and is engaged by posts 60, all of the necessary slack 58 is to be located between the posts 60 and the catheter end 50 of the tube 30.

In another embodiment of the present invention, there is provided restricting means 64 for connecting the strap 22 with the distal end of the patient's limb as shown in FIG. 1. The preferred restricting means 64 comprises a loop 66 adapted for placement over the patient's toe, or over the patient's finger as in FIG. 1. More preferably, the loop 66 is adapted for placement over the patient's thumb. Preferably, the loop 66 extends to a tail section 68 having a plurality of holes 70 spaced therealong. The tail section 68 is adjustably connectable to the strap 22 via any one of the plurality of holes 70. The holes 70 are connectable to a stud 72 affixed to the strap 22. Preferably, at least two studs 72 are affixed to the strap 22 to accommodate the attachment of the loop 66 to an appendage on either the patient's right or left hand or foot, e.g., thumb of right or left hand.

Restricting means 64 is connected to the strap 22 so as to restrict the proximal longitudinal movement of strap 22 along the patient's limb without the need for relying on the natural contours of the limb. Further, restricting means 64 is used to restrict the rotational movement of strap 22 around the patient's limb. Both longitudinal and rotational movement are made possible by the loose securement of the strap 22 around the limb. For example, when the infusion site 56 is located on the distal part of the patient's limb, e.g., on the patient's hand as shown alternatively in FIG. 1, or on the patient's foot, restricting means 64 is used to stop rotational and longitudinal movement of strap 22 before all of the slack 58 in tube 30 is used. As a further example, when the infusion site 56 is located on the proximal part of the patient's limb, e.g., on the upper part of the patient's arm as shown in FIG. 1 restricting means 64 is used to stop rotational movement of strap 22 before all of the slack 58 in tube 30 is used. Of course in the latter example, restricting means 64 will also stop longitudinal movement of strap 22 toward the infusion site 56, and can therefore be used to prevent strap 22 from reaching and interfering with the catheter 54 without reliance upon the contours of the limb.

Figures 5, 6, 7, 8:
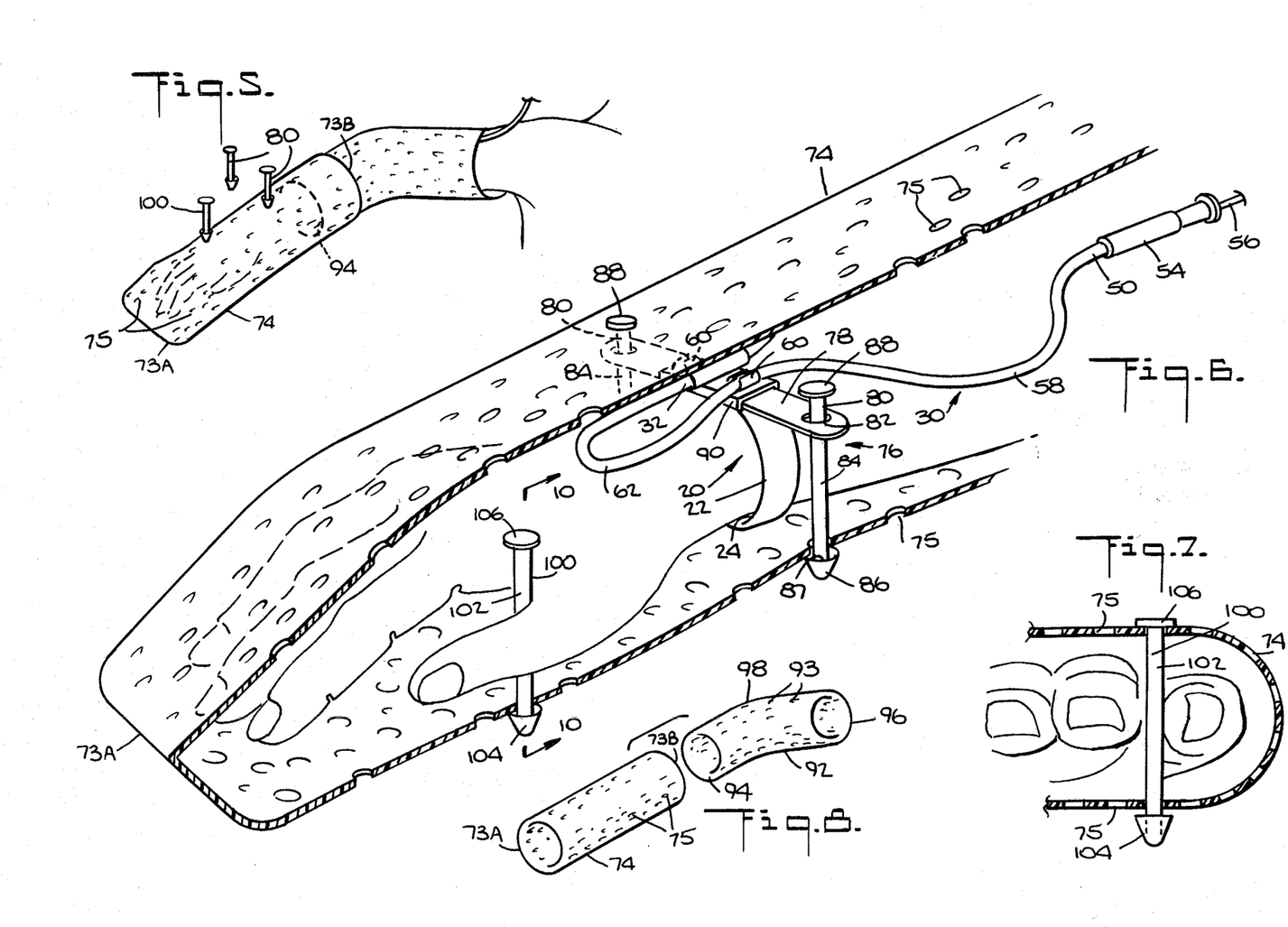
FIG. 5 illustrates a protection sleeve placed over the arm of a patient being fed intravenously.
FIG. 6 illustrates a cutaway view of an intravenous feeding device connected to a protection sleeve placed over a patient's arm.
FIG. 7 is a front view of the patient's fingers along line 10—10 in FIG. 6.
FIG. 8 illustrates a two piece sleeve for a patient's arm.

FIG. 6 illustrates a further embodiment of the present invention. Once the device 20 is secured to the patient's limb for intravenous feeding, and the catheter 54 has been inserted at the infusion site 56, the patient's limb is inserted into a protection sleeve 74 having at least its proximal end 73B open. The protection sleeve is then connected to the strap 22 by connecting means 76.

The protection sleeve 74 is preferably a tube as shown in FIG. 5, and is preferably of sufficient length to cover beyond both the infusion site 56 and the extreme distal and proximal points to which the strap 22 is able to move longitudinally along the patient's limb.

The patient's limb should fit within the protection sleeve 74 with at least some clearance between the limb and the walls of the protection sleeve 74. However, it is not desirable that such clearance be too large. The clearance should be sufficient to allow the patient some flexing movement of the limb, while at the same time preventing flexing movements that might interfere with the intravenous feeding. The protection sleeve 74 thus serves as an arm board or splint while providing a certain amount of flexing comfort. Further, a certain amount of clearance is needed to provide space for the device 20 when it is secured around the patient's limb. Still further, the clearance promotes ventilation of the enclosed limb, thereby reducing any sweating which the patient would otherwise experience with a tightly fitting device.

While clearance is needed between the limb and the walls of the protection sleeve 74, this clearance is preferably limited so as to inhibit the insertion of the patient's free hand if the patient tries to tamper with the strap 22 or the catheter 54 at the infusion site 56.

The distal end 73A of the protection sleeve 74 should preferably be closed, as shown in FIGS. 5 and 6, in order to minimize unauthorized tampering with the intravenous feeding, i.e., by the insertion of a free hand.

Figure 9:
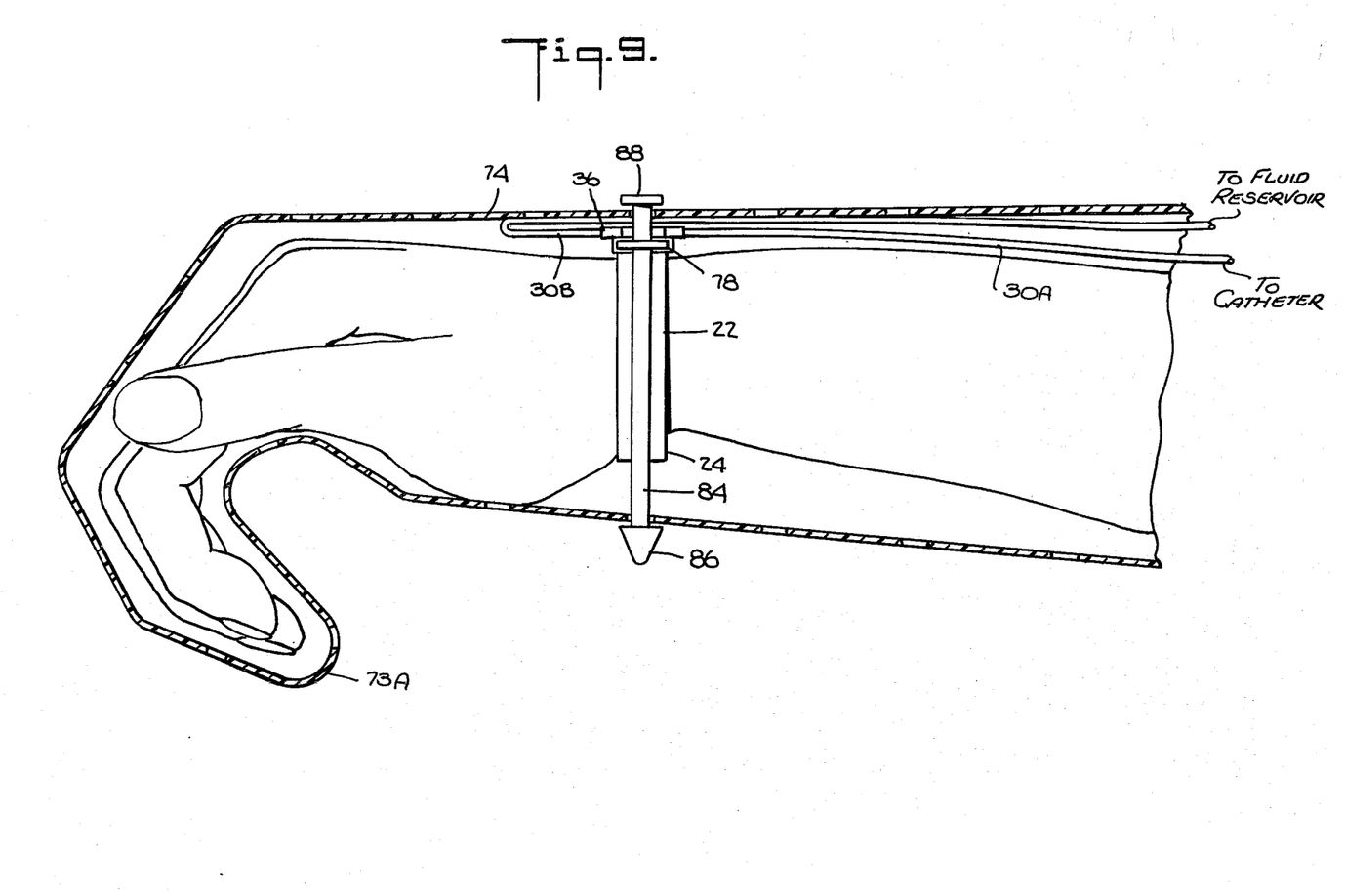
FIG. 9 illustrates a side cutaway view of a protection sleeve placed over the arm of a patient wherein the distal end of the sleeve is curved so as to accomodate the patient's fingers in a flexed position.

A protection sleeve 74, intended for use on a patient's arm, is preferably tapered at its end 73A to adapt to the flat contours of the patient's hand, as shown in FIGS. 5 and 6. Such tapering serves as a convenient means of closing the distal end 73A of the protection sleeve 74, while serving to restrict rotational movement of the patient's arm relative to the protection sleeve 74. Preferably, the distal end 73A of the protection sleeve 74 is curved so as to accommodate the fingers in a flexed position, as shown in FIG. 9. This allows for patient comfort and further restricts rotational movement of the patient's arm relative to the protection sleeve 74.

Preferably, the protection sleeve 74 is constructed of plastic materials, and more preferably is constructed of 20-30 mil polypropylene or other essentially transparent material The transparency allows medical personnel to monitor both the infusion site 56 and surrounding tissue. In addition, such plastic construction is relatively inexpensive, permitting disposal of the protection sleeve 74 and thus eliminating sterilization for subsequent patient use. Further, a plastic protection sleeve can be cut with a pair of scissors to fit the desired length for any given patient, thereby minimizing the number of sizes to be stocked by a hospital. In addition, it is preferred that the protection sleeve 74 has a plurality of holes 75 in the walls thereof, and such plastic construction readily lends itself to such manufacture. The holes 75 promote ventilation of the limb, thereby tending to maximize patient comfort.

The protection sleeve 74 should be constructed of materials such as 20-30 mil polypropylene, which are sufficient for the protection sleeve 74 to serve the functions similar to an arm board or splint. However, when the protection sleeve 74 is constructed of the more flexible materials, reinforcing means (not shown), such as a rod, may be attached to the protective sleeve 74 so as to supplement this function as an arm board or splint.

The preferred connecting means 76 for connecting the protection sleeve 74 with the strap 22 comprises a leaf 78 and a pin 80 as illustrated in FIG. 6. The leaf 78 is affixed to the strap 22 and has at least one hole 82 therein. Preferably, leaf 78 is plastic. The pin 80 comprises a shaft 84, having a barb 86 at one end and an abuttment 88 at the other end. The shaft 84 and the barb 86 are adapted to fit through at least some, and preferably all, of the plurality of holes 75 in the walls of the protection sleeve 74. The shaft 84 and the barb 86 are also adapted to fit through the hole 82 in the leaf 78. The barb 86 is adapted to prevent the pin 80 from backing out of the hole 82 in the leaf 78. Preferably, barb 86 is also adapted to prevent the pin 80 from backing out of the holes 75 in the walls of the protection sleeve 74. The abuttment 88 is adapted as not to fit through at least some of the plurality of holes 75 in the walls of the protection sleeve 74. Any of the holes 75, which might permit passage therethrough of the abuttment 88, are merely not used for insertion of the pin 80. Preferably, the abuttment 88 is adapted as not to fit through any of the holes 75.

Preferably barb 86 is a hollow polypropylene cone with the top part 87 of the cone being flexible and slightly larger than the hole 82 in the leaf 78, and also preferably slightly larger than the holes 75 in the walls of the protection sleeve 74. The shaft 84 is then affixed to the inside bottom of the barb 86. The barb 86 can thus be directed through the holes 75 and 82, with the top part 87 of the coned barb 86 contracting to allow insertion through the holes and then expanding to prevent its backing out of these holes.

Once the barb 86 is inserted through one of the holes 75 in the walls of the protection sleeve 74 and then through the hole 82 in the leaf 78, the protection sleeve 74 cannot readily be removed from the patient's limb by a patient who, without authorization of medical personnel, attempts to tamper with the intravenous feeding. Since the strap 22 cannot slide off the patient's limb, and the protection sleeve 74 is connected to the strap, the protection sleeve also cannot slide off the limb. To facilitate quick removal of the protection sleeve 74 by medical personnel in the event of an emergency, it is preferred that the entire pin 80 be constructed of plastic, such as polypropylene. Such construction permits medical personnel to cut off the abuttment 88, or the barb 86 if it extends through the walls of the protection sleeve 74, using a pair of scissors. Since the protection sleeve 74 is not damaged during its removal, it can easily be placed back on the patient using a new pin 80.

While the insertion of the barb 86 can be stopped after it passes through the hole 82 in the leaf 78, the barb can be pushed further and inserted through another hole 75 in the wall of the protection sleeve 74 which is opposite its initial insertion point, as shown in FIG. 6, thereby providing a more balanced connection as well as another item, i.e., the barb, that can be cut to provide quick access to the limb by medical personnel. When this is to be done, it is preferred that the hole 82 in the leaf 78 be larger than the holes 75 in the wall of the protection sleeve 74. This makes it easier for medical personnel to slide the barb 86 through the hole 82 in the leaf 78.

Preferably the tip of the barb 86 should be rounded and smooth to prevent snagging of the pin on the bedclothes and to prevent the pins from sticking the patient.

Preferably, the abuttment 88 is button shaped. The diameter of the abuttment is thus made larger than the diameter of the holes 75 in the walls of the protection sleeve 74 so the abuttment cannot pass therethrough.

Since the device 20 may be used without the protection sleeve 74, it is desirable in some cases that the leaf 78 be removable so as not to snag on the bedclothes and the like. To provide such removability, the strap 22 preferably has affixed thereto a complementary apertured cuff 90 for slideably receiving and overlying the leaf 78 intermediate at least two holes 82 located one at each end of the leaf 78 as shown in FIG. 1. When the protection sleeve 74 is not being used, the leaf 78 is merely removed and discarded. When the protection sleeve 74 is used, the leaf 78 is inserted into the complementary apertured cuff 90 in a position for receiving two pins 80, one through each of the holes 82 in the leaf 78 as shown in FIG. 6. The shafts 84 of each pin 80 maintain the leaf 78 within the complementary apertured cuff 90, and therefore keep the leaf connected to the device 20. When the protection sleeve 74 is not being used, an alternative to a removable leaf is shown in FIG. 3, wherein no provisions for a leaf 78 are provided at all.

When the infusion site 56 is on the proximal portion of the patient's limb, it may be desirable to use an extension sleeve 92 in conjunction with the protection sleeve 74, as shown in FIGS. 5 and 8, to more fully prevent patient access to the infusion site 56. Extension sleeve 92, having two open ends, distal end 94 and proximal end 96, is adapted to allow insertion of the patient's limb therein. Extension sleeve 92 has a bend 98 therein, coresponding generally to a slight bend in the patient's limb, i.e., a slightly bent knee or elbow. The distal end 94 of the extension sleeve 92 is adapted to fit inside the proximal end 73B of the protection sleeve 74. The use of such an extension sleeve 92 permits the patient to relax in a more natural, bent-limbed position, when such position is permissible, rather than in an essentially cramped, straight-limbed position.

Preferably, the extension sleeve 92 has a plurality of holes 93 in its walls to facilitate ventilation of the patient's limb, and, similar to the protection sleeve 74, is preferably made of plastic, such as 20–30 mil polypropylene.

Another simple means of restricting rotational movement of a patient's arm relative to the protection sleeve 74 is the insertion of another pin 100 through a hole 75 near the distal end 73A of the protection sleeve 74, as shown in FIGS. 5 and 6. The pin 100 is inserted at a point such that the shaft 102 of the pin 100 passes between two of the patient's fingers, preferably between the patient's thumb and index finger as shown in FIGS. 6 and 7. The pin is then pushed through a second hole 75 located in the opposite wall of the protection sleeve 74, thereby connecting the opposite walls of the protection sleeve 74. The pin 100 comprises a shaft 102 having a barb 104 at one end and an abuttment 106 at the other end. The shaft 102 and the barb 104 are adapted to fit through at least some, and preferably all of the holes 75 in the walls of the protection sleeve 74. The barb 104 is adapted to prevent the pin 100 from backing out of the holes 75 in the protection sleeve 74. The abuttment 106 is adapted as not to fit through at least some of the plurality of holes 75 in the walls of the protection sleeve 74. Preferably, the abuttment 106 is adapted as not to fit through any of the holes 75. Preferably, pin 100 and pin 80 are identical to each other, such that they are interchangeable for their intended functions.

While the present invention with its unique strap design, tube design, and sleeves serves to minimize the potential unauthorized or unintentional removal of the catheter 54 from the infusion site 56 on the patient's limb, it may be desired in some cases to prevent the patient from pulling the fluid reservoir 52 from its hanging position as shown in FIG. 4. One means of accomplishing such a desired result is the use of a bedrail strap 108 as illustrated in FIG. 4. Tube 30 is affixed to the bedrail strap 108 at a point between the fluid reservoir end 48 of the tube 30 and the intermediate location 32, where the tube 30 is affixed to the strap 22. Tube 30 can be so affixed to the bedrail strap by any of the means by which the tube 30 is affixed to the strap 22. Bedrail strap 108 can be attached to a bedrail 110 by any means. For example, attaching means such as the buckle 26 shown as part of strap 22 in FIG. 2 might be used. When the bedrail strap 108 is used in conjunction with the strap 22 for the patient's limb, any tension applied to tube 30 between the strap 22 and the bedrail strap 108 is transferred to the strap 22 and the bedrail strap 108 rather than the catheter 54 or the fluid reservoir 52.

The present invention provides a very flexible system for conducting intravenous therapy. The strap 22 can be used on the patient's arms or legs and can be positioned such that the tube 30 conveniently connects to the fluid reservoir 52, wherever it may be located relative to the patient, while at the same time allowing infusion at either the proximal or distal part of the limb. Without creating a tourniquet effect, the strap 22 is permitted to move longitudinally along the limb and is adjusted such that the natural contours of the limb prevent removal of the strap from the limb and interference by the strap with the infusion site 56.

The pins, in conjunction with the protection sleeve and the extension sleeve, provide a flexible system of preventing patient access to the catheter. The pins are all preferably the same size and can be used to connect various parts of the device together. The pins connect the protection sleeve 74 to the leaf 78 on the strap 22. The pins can be inserted between the fingers of the patient to restrict rotation of the patient's arm relative to the protection sleeve 74. The pins can also be used to connect the proximal end 73B of the protection sleeve to the distal end 94 of the extension sleeve via the holes in each of these. Further, where the diameter at the proximal end 73B of the protection sleeve 74 is very large relative to the patient's limb, thereby providing too large a clearance for an errant hand, the pins can be used to close the size of the opening by pinching the walls and inserting a pin through the opposite walls formed by the pinch, thereby preventing unauthorized access to the infusion site.

What is claimed is:

1. An intravenous feeding device, comprising:
a strap with fastening means, adapted for loose securement around a patient's limb, the encircling length of said strap adaptable to a position permitting longitudinal movement of said strap along the limb where the natural contours of the limb prevent removal of said strap therefrom;
a tube affixed to said strap at a location intermediate the ends of said tube, one end of said tube adapted for connection to a fluid reservoir, the other end of said tube adapted for connection to a catheter for insertion at an infusion site on the patient's limb, the segment of said tube between the intermediate location and the catheter end of said tube having sufficient slack such that the longitudinal movement of said strap away from the infusion site will be stopped by the natural contours of the patient's limb before all of the slack is used;
a protection sleeve adapted for inserting and covering the patient's limb, and means to connect said sleeve to said strap.

2. The intravenous feeding device of claim 1 wherein said protection sleeve is a plastic, essentially transparent tube of sufficient length to cover beyond both the infusion site on the limb and the extreme distal and proximal points to which said strap is able to move longitudinally along the limb.

3. The intravenous feeding device of claim 2 wherein said protection sleeve is 20–30 mil polypropylene and has a plurality of holes in its walls, and said protection sleeve is open at its proximal end and closed at its distal end, and wherein said means to connect said protection sleeve to said strap comprises a leaf affixed to said strap and having a hole therein, and a first pin having a shaft with a barb at one end and an abuttment at the other end, the shaft and barb adapted to fit through the holes in the walls of said protection sleeve and the hole in said leaf, with the barb adapted to prevent said first pin from backing out of the hole in said leaf, and the abuttment adapted as not to fit through the holes in the walls of said protection sleeve.

4. The intravenous feeding device of claim 3 wherein said first pin is plastic and said barb on said first pin is rounded.

5. The intravenous feeding device of claim 4 wherein said strap is adapted for the patient's arm and said protection sleeve is tapered toward its distal end to adapt to the flat contours of the patient's hand.

6. The intravenous feeding device of claim 5 further comprising a plastic extension sleeve open at both ends for inserting and covering the proximal portion of the patient's arm, said extension sleeve having a bend therein to generally conform to a slightly bent elbow, said extension sleeve adapted at its distal end to fit into the open proximal end of said protection sleeve.

7. The intravenous feeding device of claim 5 further comprising a second pin adapted for inserting through and connecting the opposite walls of the tapered distal end of said protection sleeve, said second pin having a shaft with a barb at one end and an abuttment at the other end, the shaft and barb of said second pin adapted to fit through the holes in the walls of said protection sleeve and between a patient's fingers, with the barb adapted to prevent said second pin from backing out of the holes in the walls of said protection sleeve, and the abuttment adapted as not to fit through the holes in the walls of said protection sleeve.

8. The intravenous feeding device of claim 7 wherein said second pin is plastic and said barb on said second pin is rounded.

9. The intravenous feeding device of claims, 1 or 8, further comprising a catheter adapted for connection to said other end of said tube.

10. An intravenous feeding device, comprising:
a strap with fastening means, adapted for loose securement around a patient's limb, the encircling length of said strap adaptable to a position permitting longitudinal movement of said strap along the limb where the natural contours of the limb prevent removal of said strap therefrom;
a tube affixed to said strap at a location intermediate the ends of said tube, one end of said tube adapted for connection to a fluid reservoir, the other end of said tube adapted for connection to a catheter for insertion at an infusion site on the proximal part of the patient's limb, the segment of said tube between the intermediate slack location and the catheter end of said tube having sufficient slack such that the longitudinal movement of said strap away from the infusion site will be stopped by the natural contours of the patient's limb before all of the slack is used; and a loop adapted for placement over a finger toe or a toe on the distal end of the patient's limb, said loop being connectable to said strap, and said loop adapted to stop rotational movement of said strap before all of the slack in the tube is used.

11. The intravenous feeding device of claim 10 wherein said loop has a tail section with a plurality of holes spaced therealong, and said strap has a stud affixed thereto for adjustably connecting said loop to said strap via any one of the plurality of holes on said tail section.

12. An intravenous feeding device, comprising:
a strap with fastening means, adapted for loose securement around a patient's limb, the encircling length of said strap adaptable to a position permitting longitudinal movement of said strap along the limb where the natural contours of the limb prevent its removal from the limb and stop the longitudinal movement of said strap before it reaches an infusion site on the limb;
a plastic leaf having a hole at each end, said strap having a complementary apertured cuff affixed thereto for slideably receiving and overlying said leaf intermediate the holes at each end of said leaf;
a tube affixed to said strap at a location intermediate the ends of said tube, one end of said tube adapted for connection to a fluid reservoir, the other end of said tube adapted for connection to a catheter for insertion at the infusion site on the patient's limb, the segment of said tube between the intermediate location and the catheter end of said tube having sufficient slack such that the longitudinal movement of said strap away from the infusion site will be stopped by the natural contours of the patient's limb before all of the slack is used;
a loop adapted for placement over one of the patient's fingers or toes, said loop having a tail section with a plurality of holes spaced therealong, said strap having two studs affixed thereto, one on each side of the complementary apertured cuff, said studs adapted to connect the loop to the strap via any one of the plurality of holes in said tail section to stop both rotational movement of said strap around the patient's limb and the longitudinal movement of said strap toward the proximal part of the patient's limb before all of the slack in said tube is used;
a plurality of upstanding posts affixed to the top of the complementary apertured cuff for receiving and engaging said tube at a point between the catheter end of said tube and the intermediate location;
a bedrail strap adapted to encircle and attach to the upstanding rails on a hospital bed, said tube being affixed to said bedrail strap intermediate said strap for the patient's limb and the end of the tube which is adapted for connection to a fluid reservoir;
a 20-30 mil polypropylene protection sleeve of tubular shape with a plurality of holes in its walls, said protection sleeve being closed at its distal end and open at its proximal end to allow insertion of the patient's limb, said protection sleeve being of sufficient length to cover beyond both the infusion site on the limb and the extreme distal and proximal points to which said strap is able to move longitudinally along the limb and two plastic pins for connecting said protection sleeve to said strap on the patient's limb, each pin having a shaft with a barb at one end and an abuttment at the other end, the barbed end of each pin being rounded, said shaft and said barb of said pins being adapted to fit through the holes in the walls of said protection sleeve and the holes in said leaf, with said barb adapted to prevent said pin from backing out of such holes, said abuttment on said pins being button-shaped and having a sufficient diameter to prevent said abuttment from passing through the holes in the wall of said protection sleeve.

13. In a method of intravenous feeding, the improvement comprising:
placing an adjustable strap with fastening means around a patient's limb;
loosely fastening said strap around the limb in a position permitting longitudinal movement of said strap along the limb but such that the natural contours of the limb prevent the removal of said strap from the limb and also such that the natural contours of the limb will stop the longitudinal movement of said strap along the limb before said strap reaches an infusion site on said limb;
providing a tube affixed to said strap at a location intermediate the ends of said tube, one end of said tube being adapted for connection to a fluid reservoir, and the other end of said tube being adapted for connection to a catheter for insertion at an infusion site on the patient's limb, the segment of said tube between the intermediate location and the catheter end of said tube having sufficient slack such that the longitudinal movement of said strap away from the infusion site will be stopped by the natural contours of the patient's limb before all of the slack is used;
inserting said catheter into the infusion site; and inserting the patient's limb into a protection sleeve which covers the limb and connecting said strap to said protection sleeve.

14. The method of claim 13 wherein said protection sleeve is a plastic, essentially transparent tube of sufficient length to cover beyond both the infusion site on the limb and the extreme distal and proximal points to which said strap is able to move longitudinally along the limb.

15. The method of claim 14 wherein said protection sleeve is 20-30 mil polypropylene and has a plurality of holes in its walls, and said protection sleeve is open at its proximal end and closed at its distal end, and wherein the step of connecting said strap to said protection sleeve comprises:
providing a leaf having a hole therein affixed to said strap;
providing a first pin having a shaft with a barb at one end and an abuttment at the other end, the shaft and barb being adapted to fit through the holes in the walls of said protection sleeve and the hole in said leaf, with the barb being adapted to prevent said first pin from backing out of the hole in said leaf, and the abuttment being adapted as not to fit through the holes in the walls of said protection sleeve; and
inserting the barbed end of said first pin through a hole in the wall of said protection sleeve and through the hole in said leaf.

16. The method of claim 15 wherein said strap is loosely fastened around the patient's arm, and wherein said protection sleeve is tapered toward its distal end to adapt to the flat contours of the patient's hand, and further comprising:

providing a second pin having a shaft with a barb at one end and an abutment at the other end, the shaft and barb of said second pin being adapted to fit through the holes in the walls of said protection sleeve, with the barb being adapted to prevent said second pin from backing out of the holes in the walls of said protection sleeve, and the abutment being adapted as not to fit through the holes in the walls of said protection sleeve;

inserting the barbed end of said second pin through a hole in the wall of said protection sleeve toward the distal end of said protection sleeve; and continuing the insertion of the barbed end of said second pin between two of the patient's fingers and through a hole in the opposite wall of said protection sleeve.

17. In a method of intravenous feeding, the improvment comprising:

placing an adjustable strap with fastening means around a patient's limb;

loosely fastening said strap around the limb in a position so that there is longitudinal movement of said strap along the limb but such that the natural contours of the limb prevent the removal of said strap from the limb;

providing a tube affixed to said strap at a location intermediate the ends of said tube, one end of said tube being adapted for connection to a fluid reservoir, and the other end of said tube being adapted for connection to a catheter for insertion at an infusion site on the patient's limb, the segment of said tube between the intermediate location and the catheter end of said tube having sufficient slack such that the longitudinal movement of said strap away from the infusion site, which is on the proximal part of the patient's limb, will be stopped by the natural contours of the patient's limb before all of the slack is used; and placing a loop connected to said strap over one of the patient's fingers or toes at the distal end of the patient's limb so as to stop rotational movement of said strap before all of the slack in said tube is used.

18. The method of claim 17 wherein said loop is connected to said strap by providing said loop with a tail section having a plurality of holes spaced therealong; providing said strap with a stud affixed thereto; and placing said stud through one of the plurality of holes on said tail section.

19. In a method of intravenous feeding, the improvement comprising:

placing an adjustable strap with fastening means around a patient's limb, said strap having affixed thereto both a leaf with a hole at opposite ends and a plurality of upstanding posts for receiving and engaging tubing;

loosely fastening said strap around the limb in a position permitting longitudinal movement of said strap along the limb, but such that the natural contours of the limb prevent the removal of said strap from the limb and stop the longitudinal movement of said strap before said strap reaches an intended infusion site on the limb;

providing a tube affixed to said strap at a location intermediate the ends of said tube, one end of said tube being connected to a fluid reservoir placed behind the patient, the other end of said tube being connected to a catheter, the segment of said tube between the intermediate location and the catheter being doubled back and inserted into the upstanding posts on said strap, the segment of said tube between the upstanding posts on said strap and the catheter having sufficient slack such that the longitudinal movement of said strap away from the infusion site will be stopped by the natural contours of the limb before all of the slack is used;

connecting a loop placed over one of the patient's fingers or toes to said strap to restrict rotational movement of said strap around the patient's limb and the longitudinal movement of said strap toward the proximal part of the patient's limb before all of the slack in said tube is used;

inserting the catheter into the infusion site on the patient's limb;

providing a 20–30 mil polypropylene protection sleeve having a plurality of holes in its walls, said protection sleeve being closed at its distal end and open at its proximal end to allow insertion of the patient's limb, said protection sleeve being of sufficient length to cover beyond both the infusion site on the limb and the extreme distal and proximal points to which said strap is able to move longitudinally along the limb;

inserting the patient's limb into said protection sleeve to a point covering beyond both the infusion site on the limb and the extreme distal and proximal points to which said strap is able to move longitudinally along the limb;

connecting said protection sleeve to said strap with two plastic pins each having a barb at one end and an abutment at the other end, the barbed end of each pin being inserted through a hole in the walls of said protection sleeve and through one of the two holes in said leaf, and further through a hole in the opposite wall of said protection sleeve, the barb being adapted to prevent the pin from backing out of the holes in the walls of the protection sleeve, and the abutment being adapted as not to fit through the holes in the walls of said protection sleeve; and affixing said tube, at a point between the fluid reservoir end of said tube and the protection sleeve, to a bedrail on the patient's bed.

* * * * *